United States Patent [19]

Florkiewicz et al.

[11] Patent Number: 5,332,804
[45] Date of Patent: Jul. 26, 1994

[54] HIGH MOLECULAR WEIGHT HUMAN ANGIOGENIC BASIC FIBROBLAST GROWTH FACTORS

[75] Inventors: Robert Z. Florkiewicz, Poway, Calif.; Andreas Sommer, Boulder, Colo.

[73] Assignee: Synergen, Inc., Boulder, Colo.

[21] Appl. No.: 687,496

[22] Filed: Apr. 16, 1991

Related U.S. Application Data

[62] Division of Ser. No. 267,966, Nov. 7, 1988, abandoned.

[51] Int. Cl.[5] .................. A61K 37/36; C07K 13/00
[52] U.S. Cl. ...................... 530/399; 530/412
[58] Field of Search .................. 530/399, 412

[56] References Cited

PUBLICATIONS

Klagsburn et al. *Proc. Natl Acad Sci USA* 84:1839–1843 (1987).
Abraham et al. *The Embo J.* 5(10):2523–28 (1986).
Presta et al. *Molecular & Cellular Biol.* 6(11):4060–66 (1986).
Hann et al. *Cell* 52:185–195 (Jan. 29, 1988).
Sommer et al. *Biochem & Biophys Res Comm* 144(2):543–50 (1987).
Moscatelli et al. *Proc Natl Acad Sci USA* 83:2091–95 (1986).
Klagsburn et al. *Proc Natl Acad Sci USA* 83:2448–52 (1986).
Moscatelli et al *Proc Natl Acad Sci USA* 84:5778–82 (1987).
Moscatelli et al *Biochimie* 70:83–87 (Jan., 1988).
Ueno et al. *Biochem Biophys Res Comm* 138(2):580–88 (1986).
Klagsburn et al. in *Angiogenesis Mechanisms & Pathobiology* ed. Rifkin, D. B., Cold Spring Harbor:1987.
Kurokawa et al. *FEBS* 213(1):189–194 (1987).
Bowie et al. *Science* 247:1306–1310 (1990).

*Primary Examiner*—Robert J. Hill, Jr.
*Assistant Examiner*—Shelly Guest Cermak
*Attorney, Agent, or Firm*—Beaton & Swanson

[57] ABSTRACT

High molecular weight forms of therapeutic proteins are disclosed which are single-polypeptide-chain proteins that contain the same or similar therapeutic activity as the therapeutic protein. In particular, high molecular weight forms of the human bFGF angiogenic factor are disclosed which are single-polypeptide-chain proteins having at least one active site possessing an activity selected from the group consisting of mitogenic activity, chemotactic activity, angiogenic activity, neurotrophic activity, the ability to stimulate protease synthesis and combinations thereof. The high molecular weight angiogenic factors exhibit substantial homology to and are immunologically equivalent to the native high molecular weight forms isolatable from human hepatoma cells. The high molecular weight angiogenic factors are produced by DNA translation initiating at non-ATG codons and incorporate additional polypeptide sequences N-terminal to the human bFGF factor. The amino acid sequences of the high molecular weight angiogenic factors and the oligonucleotide sequence that translate to form the high molecular weight bFGF proteins are also disclosed. Methods for isolating the high molecular weight angiogenic factors from human hepatoma cell line SK-HEP-1 and producing the proteins by recombinant DNA techniques are also described.

5 Claims, No Drawings

HIGH MOLECULAR WEIGHT HUMAN ANGIOGENIC BASIC FIBROBLAST GROWTH FACTORS

This is a division of copending application Ser. No. 07/267,966, filed on Nov. 7, 1988, now abandoned.

BACKGROUND OF THE INVENTION

The process of angiogenesis involves a complex interplay of biological functions including (1) "activation" of quiescent endothelium, (2) vascular endothelial cell invasion of basement membranes and adjacent tissues and (3) capillary tube formation. These events can be stimulated by a number of different angiogenic factors. Angiogenic factors can, however, have quite different effects on capillary endothelial cell locomotion and proliferation "in vitro," two of the key events necessary for the formation of new capillary blood vessels. Some angiogenic factors stimulate endothelial cell locomotion or proliferation, or both. In contrast, others have no effect, or inhibit endothelial cell proliferation "in vitro." These findings suggest that various angiogenic factors may operate either directly or indirectly when evaluated according to their putative targets.

Human basic fibroblast growth factor (bFGF) is classified as a "direct" angiogenic factor. A human bFGF molecule that was purified from placenta ("placental bFGF") was shown to (a) stimulate capillary endothelial cell proliferation, (b) to stimulate chemotaxis in capillary endothelial cells and (c) to stimulate these same cells to produce plasminogen activator and latent collagenase. Moscatelli et al., *Proc. Natl. Acad. Sci. USA*, 1986, Vol. 83, p. 2091. "In vivo," the plasminogen activator can convert the zymogen plasminogen to active plasmin, a protease of wide specificity. The plasmin can then convert latent collagenase to active collagenase. Thus, under the influence of the placental bFGF, capillary endothelial cells can generate two proteases that are able to degrade most of the proteins in surrounding tissues, which would allow the endothelial cells to penetrate the tissues. Indeed, the purified placental bFGF protein was shown to be angiogenic "in vivo." See Moscatelli supra; squires et al., *J. Bio. Chem.*, 1988, in press (est. December 1988 publication). The isolation, structure and properties of the human placenta bFGF have been described in U.S. Pat. No. 4,994,559 of Moscatelli et al., which is incorporated herein in its entirety by this reference.

An angiogenic protein in a pure form, such as the placental bFGF molecule just described, can be developed into a therapeutically valuable material. Because of the biological properties of the placental bFGF, the protein, when properly administered, can have beneficial effects in the healing of wounds and bone defects, in the repair of cardiovascular damage, repair of arteriosclerotic lesions and endothelialization of synthetic vascular grafts. In addition, the placental bFGF has been shown to have neurotrophic properties which might be beneficial in the treatment of neurological disorders of diverse origins.

Several proteins have been identified which have been referred to as "angiogenic factors." Many of these proteins were isolated from nonhuman sources. There is reason to believe that angiogenic factors isolated from nonhuman sources would not be suitable for use as therapeutic agents in humans due to the potential for adverse immunological reaction in response to a foreign protein.

The nucleotide sequence of a cDNA encoding the human bFGF protein was first published by Abraham. See Abraham et al., *EMBO*, 1986, Vol. 5, pp. 2523-28. Based on the position of a single putative initiator methionine codon in the cDNA, these authors predicted that the bFGF gene product would consist of a protein of 154 amino acids ("bFGF-18"). Sommer and coworkers have shown, however, that the bFGF preparation isolated from human placenta contained a bFGF species that was N-terminally extended relative to the gene product that was predicted by Abraham et al. from the bFGF cDNA. See Sommer et al., *Biochem. Biophys. Res. Commun.*, 1987, Vol. 144, pp. 543-550.

These findings suggested the existence of multiple forms of human bFGF angiogenic factors that have not yet been described.

Based on this framework of research, the present inventors sought and discovered three new molecular forms of human bFGF classified here according to their approximate molecular size in kilodaltons (kD) as bFGF-22, bFGF-23 and bFGF-24. Collectively, the three new proteins will be referred to as higher molecular weight bFGFs (hmwbFGFs) in contrast to the previously characterized and in the literature described bFGF molecules of approximate molecular weight of 18 kD (bFGF-18) and the placental bFGF species which contains two additional amino acids N-terminal to bFGF-18 initiated methionine.

The hmwbFGF's are substantially homologous to those isolatable from the human hepatoma cell line SK-HEP-1, and have at least one active site possessing an activity selected from the group consisting of mitogenic activity, chemotactic activity, angiogenic activity, the ability to stimulate protease synthesis, and combinations thereof.

In addition to discovering the hmwbFGF's, the present inventors have also discovered the first example of a normal animal cell gene initiating protein synthesis in vivo at a non-ATG codon. Although non-ATG initiation has been described in procaryotic cell genes, there is only one previous report of animal cell genes exhibiting this behavior. Hann et al., Cell, 1988, Vol. 52 pp. 185-189. Hann has reported, using in vitro translations, that the cMYC proto-oncogene also appears to utilize non-ATG codons for translation initiation.

The existence of higher molecular weight forms of bFGF in which translation was initiated at non-ATG codons suggests that similar higher molecular weight species may exist for other human proteins of therapeutic value. The higher molecular weight forms of the protein may have similar, enhanced or even new therapeutic qualities than the parent protein. Recognizing that translational initiation may also begin at a non-ATG codon prior to an identified putative (ATG) initiator will allow researchers to seek higher molecular weight forms of many proteins. Presumably, higher molecular weight forms of active proteins, if any, will possess similar therapeutic activities while also possessing unknown additional benefits or qualities. The additional amino-terminal peptide segments may be beneficial in altering or shutting off various active sites in the proteins, or in helping control the mobility of the protein or direct its location within or to the outside of the cell. The present invention includes high molecular weight forms of therapeutic proteins that are synthesized in vivo by translation initiation from non-ATG codons, in addition to the specific example of hmwbFGF's.

The preferred hmwbFGF angiogenic factors according to the present invention have the bFGF-18 core amino acid sequence shown as follows:

bFGF-18
M—A—A—G—S—I—T—T—L—P—A—L—P—E—D—G—G—S—G—A—
F—P—P—G—H—F—K—D—P—K—R—L—Y—C—K—N—G—G—F—F—
L—R—I—H—P—D—G—R—V—D—G—V—R—E—K—S—D—P—H—I—
K—L—Q—L—Q—A—E—E—R—G—V—V—S—I—K—G—V—C—A—N—
R—Y—L—A—M—K—E—D—G—R—L—L—A—S—K—C—V—T—D—E—
C—F—F—F—E—R—L—E—S—N—N—Y—N—T—Y—R—S—R—K—Y—
T—S—W—Y—V—A—L—K—R—T—G—Q—Y—K—L—G—S—K—T—G—
P—G—Q—K—A—I—L—F—L—P—M—S—A—K—S.

In addition, peptides having the sequences

L—G—G—R—G—R—G—R—A—P—E—R—V—G—G—R—G—R—G—R—
G—T—A—A—P—R—A—A—P—A—A—R—G—S—R—P—G—P—A—G—T

L—P—G—G—R—L—G—G—R—G—R—G—R—A—P—E—R—V—G—G—
R—G—R—G—R—G—T—A—A—P—R—A—A—P—A—A—R—G—S—R—
P—G—P—A—G—T

L—G—A—R—G—R—A—L—P—G—G—R—L—G—G—R—G—R—G—R—
A—P—E—R—V—G—G—R—G—R—G—R—G—T—A—A—P—R—A—A—
P—A—A—R—G—S—R—P—G—P—A—G—T are present in the polypeptides outside the core sequence. Among the particularly preferred hmwbFGF angiogenic factors are the following sequences:

L—G—G—R—G—R—G—R—A—P—E—R—V—G—G—R—G—R—G—R—
G—T—A—A—P—R—A—A—P—A—A—R—G—S—R—P—G—P—A—G—
T—bFGF-18

L—P—G—G—R—L—G—G—R—G—R—G—R—A—P—E—R—V—G—G—
R—G—R—G—T—A—A—P—R—A—A—P—A—A—R—G—S—R—
P—G—P—A—G—T—bFGF-18

L—G—A—R—G—R—A—L—P—G—G—R—L—G—G—R—G—R—G—R—
A—P—E—R—V—G—G—R—G—R—G—R—G—T—A—A—P—R—A—A—
P—A—A—R—G—S—R—P—G—P—A—G—T—bFGF-18

The amino acids represented by the foregoing abbreviations are set forth in the description of the preferred embodiments below.

The relevant nucleotide sequence of the cDNA clone used to generate RNA for translation leading to the hmwbFGF's and the bFGF18 factor is as follows:

181                          201
CGG CCG AGC GGC TCG AGG CTG GGG GAC CGC

228
GGG CGC GGC CGC GCG CTG CCG GGC GGG AGG 243                250
CTG GGG GGC CGG GGC CGG GGC CGT CCC CCG

300
GAG CGG GTC GGA GGC CGG GGC CGG GGC CGG

GGG ACG GCG GCT CCC CGC GCG GCT CCA GCG

350
GCT CGG GGA TCC CGG CCG GGC CCC GCA GGG

365
ACC ATG GCA — — — — — — — — — — — — — — TGA
bFGF-18

The bFGF-18 polypeptide is initiated at ATG 365, although, as described previously, the placental bFGF has a two-amino acid amino-terminal extension unto themethionine formed by the ATG initiator. The nucleotide numbering begins at the first nucleic acid of the cDNA clone that has been identified as expressing the bFGF angiogenic factor. The nucleotide sequence of the cDNA clone used to generate RNA for translation leading to the bFGF-18 factor is as follows:

bFGF-18
ATG GCA GCC GGG AGC ATC ACC ACG CTG CCC
GCC TTG CCC GAG GAT GGC GGC AGC GGC GCC
TTC CCG CCC GGC CAC TTC AAG GAC CCC AAG
CGG CTG TAC TGC AAA AAG GGG GGC TTC TTC
CTG CGC ATC CAC CCC GAC GGC CGA GTT GAC
GGG GTC CGG GAG AAG AGC GAC CCT CAC ATC
AAG CTA CAA CTT CAA GCA GAA GAG AGA GGA
GTT GTG TCT ATC AAA GGA GTG TGT GCT AAC
CGT TAC CTG GCT ATG AAG GAA GAT GGA AGA
TTA CTG GCT TCT AAA TGT GTT ACG GAT GAG
TGT TTC TTT TTT GAA CGA TTG GAA TCT AAT
AAC TAC AAT ACT TAC CGG TCA AGG AAA TAC
ACC AGT TGG TAT GTG GCA CTG AAA CGA ACT
GGG CAG TAT AAA CTT GGA TCC AAA ACA GGA
CCT GGG CAG AAA GCT ATA CTT TTT CTT CCA

-continued
ATG TCT GCT AAG AGC TGA TTT TAA

The preferred hmwbFGF's are produced by translation initiation beginning at codons prior to ATG 365. The particularly preferred hmwbFGF's are produced by translation initiation at CTG 201, CTG 228 and CTG 243. The nucleic acids represented by the foregoing abbreviations are set forth in the Description of the Preferred Embodiments below.

Furthermore, in accordance with the present invention, pharmaceutical compositions containing, as at least one of the active ingredients, an angiogenic factor in accordance with the present invention as set forth herein are disclosed.

It is to be understood that both the foregoing general description and the following detailed descriptions are exemplary and exemplary only and are not restrictive of the invention, as claimed.

DESCRIPTION OF THE PREFERRED EMBODIMENTS

The principles of the present invention will be explained by this detailed description of the preferred embodiments, together with the following examples.

The present invention relates to therapeutic proteins which may be isolated and separated via standard laboratory techniques. In particular, the present invention relates to angiogenic factors which have been isolated and separated and identified by Western blot analysis. Preferably, the angiogenic factors of the present invention are single-polypeptide-chain proteins which are substantially homologous to, immunologically equivalent to, and, most preferably, biologically equivalent to, native angiogenic factors isolatable from human hepatoma cell line SK-HEP-1. The human hepatoma cell line SK-HEP-1 is a commonly used strain of human cell tissue familiar to those skilled in the art and available through various biochemical supply houses. By "biologically equivalent," as used throughout this specification and claims, it is meant that the composition of the present invention possesses mitogenic, chemotactic, protease synthesis stimulation, angiogenic or other properties in the same manner, but not necessarily to the same degree, as the native angiogenic factors.

By "substantially homologous," as used throughout the ensuing specification and claims and when referring to any protein, is meant a degree of homology to the native angiogenic factors or therapeutic protein in excess of that displayed by any previously reported, purified, substantially homologous angiogenic factor or therapeutic protein composition. Preferably, the degree of homology is in excess of 50%, preferably 60%, and more preferably 75%, with particularly preferred proteins being in excess of 85% or 90% homologous with the native protein. The degree of homology as described above is calculated as the percentage of amino acid residues found in the smaller of the two sequences that align with identical amino acid residues in the sequences being compared when four gaps in a length of 100 amino acids may be introduced to assist in that alignment as set forth by Dayboll, M. O. in Atlas of Protein Sequences and Structure, Vol. 5, page 124 (1972), National Biochemical Research Foundation, Washington, D.C., specifically incorporated herein by this reference.

By "substantially homologous," as used throughout the ensuing specifications and claims and when referring to any oligonucleotide sequence, is meant a degree of homology to the native nucleic acid sequence such that the proteins translated from said sequence will be substantially homologous to the proteins produced by the native nucleic acid sequence.

As described herein, the angiogenic factors and therapeutic proteins of the present invention are either isolated from a human source or are synthetic polypeptides. The term "synthetic" polypeptide is intended to mean an amino acid sequence which has not previously been isolated from nature in a substantially purified form. This definition includes, among other things, polypeptides created by recombinant-DNA methods or synthesized in whole or in part in vitro. In particular, synthetic polypeptides are contemplated in which the most preferred amino acid sequences set forth below are deviated from at one to several amino acids.

By "therapeutic protein," as used throughout the ensuing specification and claims, is meant any naturally occurring human protein comprising a single-polypeptide-chain and possessing valuable biological properties that may be useful in the treatment of diseases or in preventive medicine. This invention relates to all high molecular weight forms of said therapeutic proteins that are formed by in vivo translation initiation at a non-ATG codon, and methods for isolating the same.

The preferred angiogenic factors of the present invention have been discovered in human hepatoma cell line SK-HEP-1 extracts and, for the first time, have been separated from the bFGF-18 protein and each other. For the purposes of the present application, "pure form" or "purified form," when used to refer to any angiogenic factor disclosed herein, shall mean substantially free of other human proteins that are not angiogenic factors. Preferably, the angiogenic factors of the present invention are at least 50% pure, more preferably 70% pure and even more preferably 80% or 90% pure.

The angiogenic factors of the present invention may be isolated from human hepatoma cell line SK-HEP-1 by the method comprising: (a) lysing the human cell line SK-HEP-1 cells; (b) isolating the angiogenic factors by fractionating the proteinaceous material in the mixture; (c) identifying the fractions which possess placental bFGF immunological crossreactivity and which do not exclusively contain the bFGF-18 angiogenic factor; and (d) concentrating said fractions.

In a preferred embodiment, the SK-HEP-1 cells are lysed in a buffer including, among other things, 1% NP40. NP40 is a detergent commonly used in microbiological preparations consisting of an octyl phenol - ethylene oxide condensate containing an average of nine moles of ethylene oxide per mole of phenol, and is available from Sigma Chemical Company. Prior to fractionating the proteinaceous material found in the cells, all nuclei and debris are removed by centrifugation. The proteinaceous material present in the SK-HEP-1 cells is fractionated using conventional chromatographic techniques well known to those skilled in the art. In one embodiment, the proteinaceous material is fractionated using heparin-sepharose affinity chromatography, and further separated by gel electrophoresis.

Fractions obtained via the above-described fractionating techniques are screened for the presence of placental bFGF immunological crossreactivity. When utilizing gel electrophoresis, the electrophoresis is accomplished using 12% SDS-PAGE (Sodium Dodecyl Sulfate - Polyacrylamide Gel Electrophoresis) and the proteins are Western-blotted to nitrocellulose and detected with anti-placental FGF antibodies. This technique enables the separation of hmwbFGF's from each other and from the bFGF-18 factor, and indicates the presence of 22 kD, 23 kD and 24 kD molecular weight proteins that are reactive with the anti-placental FGF antibodies.

The present inventors have identified and isolated the hmwbFGF's in a purified form, and in a form substantially free of human proteins that are not angiogenic factors, for the first time. Isolation and separation of the proteins via heparin-sepharose chromatography and gel electrophoresis was a prerequisite step in establishing the sequence of the hmwbFGF's. This information, combined with knowledge of the primary structure of the cDNA described above, and experiments establishing the existence of non-ATG translation initiator codons, enabled the inventors to establish the sequence of each of the hmwbFGF's.

The structures given for the preferred angiogenic factors of this invention are determined by extrapolating from the known structure of the cDNA nucleotide sequence. It is, however, quite likely that post-translational modifications to the amino acid sequences set forth will occur. The existence of post-translational modifications to the initially translated protein means that the hmwbFGF proteins isolatable from human hepatoma cell line SK-HEP-1 will be substantially homologous but not necessarily identical to the sequences set forth below.

The hmwbFGF angiogenic factors of the present invention have the following bFGF-18 core sequence:

bFGF-18
M—A—A—G—S—I—T—T—L—P—A—L—P—E—D—G—G—S—G—A—
F—P—P—G—H—F—K—D—P—K—R—L—Y—C—K—N—G—G—F—F—
L—R—I—H—P—D—G—R—V—D—G—V—R—E—K—S—D—P—H—I—
K—L—Q—L—Q—A—E—E—R—G—V—V—S—I—K—G—V—C—A—N—
R—Y—L—A—M—K—E—D—G—R—L—L—A—S—K—C—V—T—D—E—
C—F—F—F—E—R—L—E—S—N—N—Y—N—T—Y—R—S—R—K—Y—
T—S—W—Y—V—A—L—K—R—T—G—Q—Y—K—L—G—S—K—T—G—
P—G—Q—K—A—I—L—F—L—P—M—S—A—K—S.

In addition, peptides having the sequences

L—G—G—R—G—R—G—R—A—P—E—R—V—G—G—R—G—R—G—R—
G—T—A—A—P—R—A—A—P—A—A—R—G—S—R—P—G—P—A—G—T

L—P—G—G—R—L—G—G—R—G—R—G—R—A—P—E—R—V—G—G—
R—G—R—G—R—G—T—A—A—P—R—A—A—P—A—A—R—G—S—R—
P—G—P—A—G—T

L—G—A—R—G—R—A—L—P—G—G—R—L—G—G—R—G—R—G—R—
A—P—E—R—V—G—G—R—G—R—G—R—G—T—A—A—P—R—A—A—
P—A—A—R—G—S—R—P—G—P—A—G—T are present amino-terminal to the core sequence. Particularly preferred hmwbFGF angiogenic factors have the following sequences kD-22
L—G—G—R—G—R—G—R—A—P—E—R—V—G—G—R—G—R—G—R—
G—T—A—A—P—R—A—A—P—A—A—R—G—S—R—P—G—P—A—G—
T—bFGF-18 kD-23
L—P—G—G—R—L—G—G—R—G—R—G—R—A—P—E—R—V—G—G—
R—G—R—G—R—G—T—A—A—P—R—A—A—P—A—A—R—G—S—R—
P—G—P—A—G—T—bFGF-18 kD-24
L—G—A—R—G—R—A—L—P—G—G—R—L—G—G—R—G—R—G—R—
A—P—E—R—V—G—G—R—G—R—G—R—G—T—A—A—P—R—A—A—
P—A—A—R—G—S—R—P—G—P—A—G—T—bFGF-18

The foregoing abbreviations correspond to the standard abbreviations for amino acid residues as set forth in, for example, *Biochemistry* by A. L. Lehninger, 2nd ed., Worth Publishers, Inc., New York (1975), p. 72.

The hmwbFGF angiogenic factors of the present invention may also be produced and isolated in a purified form by recombinant DNA techniques, by the method comprising: (a) isolating a DNA sequence that encodes the ultimate translation of the hmwbFGF's; (b) inserting the DNA sequence into a vector capable of expression in a host microorganism; (c) transfecting the vector containing the desired DNA sequence into a host organism capable of expressing the proteins; (d) expressing the hmwbFGF angiogenic factors from the transfected organism; and (e) in either order, isolating and purifying the desired proteins.

In a preferred embodiment, the host organism is COS-1 cells, and the vector utilized is pJC119. These are commonly used biological reagents familiar to those skilled in the art, and are available through various biochemical supply houses. In addition, the DNA contains oligonucleotide sequences the same or substantially homologous to the following:

```
CGG CCG AGC GGC TCG AGG CTG GGG GAC CGC
GGG CGC GGC CGC GCG CTG CCG GGC GGG AGG
CTG GGG GGC CGG GGC CGG GGC CGT CCC CCG
GAG CGG GTC GGA GGC CGG GGC CGG GGC CGG
```

```
                           -continued
       GGG ACG GCG GCT CCC CGC GCG GCT CCA GCG
       GCT CGG GGA TCC CGG CCG GGC CCC GCA GGG
       ACC ATG GCA GCC GGG AGC ATC ACC ACG CTG CCC
       GCC TTG CCC GAG GAT GGC GGC AGC GGC GCC
       TTC CCG CCC GGC CAC TTC AAG GAC CCC AAG
       CGG CTG TAC TGC AAA AAG GGG GGC TTC TTC
       CTG CGC ATC CAC CCC GAC GGC CGA GTT GAC
       GGG GTC CGG GAG AAG AGC GAC CCT CAC ATC
       AAG CTA CAA CTT CAA GCA GAA GAG AGA GGA
bFGF-18 GTT GTG TCT ATC AAA GGA GTG TGT GCT AAC
       CGT TAC CTG GCT ATG AAG GAA GAT GGA AGA
       TTA CTG GCT TCT AAA TGT GTT ACG GAT GAG
       TGT TTC TTT TTT GAA CGA TTG GAA TCT AAT
       AAC TAC AAT ACT TAC CGG TCA AGG AAA TAC
       ACC AGT TGG TAT GTG GCA CTG AAA CGA ACT
       GGG CAG TAT AAA CTT GGA TCC AAA ACA GGA
       CCT GGG CAG AAA GCT ATA CTT TTT CTT CCA
       ATG TCT GCT AAG AGC TGA TTT TAA
```

The inventors established the non-ATG codon initiation of translation by synthesizing nucleic acid sequences that had been altered at the proposed initiation sites. By synthesizing an oligonucleotide sequence, in all other ways identical to that naturally occurring segment that translates the hmwbFGF and bFGF-18 proteins, in which one nucleic acid is replaced by a different nucleic acid, the three nucleic acid codon in which that nucleic acid occurs will translate to a different amino acid. If the altered codon is not a translation initiator codon, generally the nucleic acid segment will still produce a protein (or proteins in this case) that is identical to the native protein but for the one amino acid difference. If, however, the initiator codon is altered, translation will not occur from that site. It is via these techniques that the inventors of the present invention have established the presence of non-ATG initiators leading to active higher molecular weight forms of the bFGF angiogenic factor.

The oligonucleotide structure giving rise to the hmwbFGF's and the bFGF-18 factor is as follows:

```
181                      201
CGG CCG AGC GGC TCG AGG CTG GGG GAC CGC

228
GGG CGC GGC CGC GCG CTG CCG GGC GGG AGG 243       250
CTG GGG GGC CGG GGC CGG GGC CGT CCC CCG

300
GAG CGG GTC GGA GGC CGG GGC CGG GGC CGG

GGG ACG GCG GCT CCC CGC GCG GCT CCA GCG

350
GCT CGG GGA TCC CGG CCG GGC CCC GCA GGG

365
ACC ATG GCA --------------TGA
              bFGF-18
```

The abbreviations used herein correspond to the abbreviations for the nucleic acids as set forth in, for example, *Biochemistry* by A. L. Lehninger, 2nd ed. Worth Publishers, Inc , New York (1975), pages 310–318.

By use of the "shut-off" initiator technique, the inventors of the present invention have also been able to show that the hmwbFGF's have substantially the same mitogenic activity as the bFGF-18 protein. Altering the ATG-365 codon, the inventors shut off production of bFGF-18 and obtained hmwbFGF's free of bFGF-18. Comparative mitogenic activity studies, based on relative concentrations, indicated that the hmwbFGF's have very similar mitogenic activity to bFGF-18. Of course, the hmwbFGF's studied for this experiment are homologs of the most preferred structures due to the amino acid substitution for the methionine at the bFGF-18 initiation site.

The inventors of the present invention have also established that the mitogenic activity of the hmwbFGF's is equivalent to that of the bFGF-18 protein by synthesizing and translating from a "frame shifted" cDNA oligonucleotide segment. Placing a single additional nucleic acid into the nucleic acid sequence just prior to the segment that translates the basic bFGF-18 protein shifts the three amino acid pairing found in all subsequent codons. Such a "frame shift" alters the protein translated from the oligonucleotide at the point where the added nucleic acid is entered into the cDNA. Via this technique, the inventors of the present invention were able to show that the mitogenic active site of the hmwbFGF's was substantially equivalent to that of the bFGF-18 protein.

The high molecular weight therapeutic proteins of the present invention are contemplated for therapeutic purposes similar to those for which the respective therapeutic proteins are valuable. In particular, the angiogenic factors of the present invention and its analogs as disclosed herein are contemplated for human and veterinary uses in the form of pharmaceutical products possessing mitogenic, chemotactic, neurotrophic or angiogenic properties or the ability to stimulate protease synthesis. It is expected that pharmaceutical preparations containing, as at least one of the active ingredients, one of the angiogenic factors of the present invention. The preparations would also contain appropriate pharmaceutically acceptable carrier, diluents, fillers, binders and other excipients depending on the dosage form contemplated. For oral administration, steps must be taken to prevent degradation of the active protein in the digestive tract. Enteric coated dosage forms are thus contemplated as one form suitable for oral administration. If parenteral administration is chosen, the preparation may contain a water or saline solution or other pharmaceutically acceptable suspension agent. Generally, it would be preferred that a preparation intended for parenteral administration contain sodium chloride or glycerol in sufficient concentrations to make the overall preparation isotonic to body fluids. It is also contemplated that the pharmaceutical preparations containing the angiogenic factors of the present invention be administered locally, as by injection or topical application, for treatment of wounds, surgical incisions or skin ulcers. Additionally, incorporation of the angiogenic factors into a slow release implant device is contemplated for administration to regenerate the blood supply to the heart after a myocardial infarction.

The calculations necessary to determine the appropriate dosage for treatment of the above-mentioned disorders and appropriate for use with the described delivery methods are routinely made by those of ordinary skill in the art and are within the ambit of tasks routinely performed by them without undue experimentation, especially in light of standard assays and assays disclosed herein. These dosages may be ascertained through use of established assays for determining dosages utilized in conjunction with appropriate dose-response data.

It is understood that the application of the teachings of the present invention to a specific problem or environment will be within the capabilities of one having ordinary skill in the art in light of the teachings contained herein. Examples of the products of the present invention and representative processes for their isolation, identification and manufacture appear in the following examples.

EXAMPLE 1

Purification of hmwbFGF's from human hepatoma cell line SK-HEP-1

Human hepatoma SK-HEP-1 cells were lysed in buffer containing 400 mM NaCl, 1 uM MgCl, 50 mM Tris pH 7.5, 1% NP40 and 1uM PMSF (phenylmethyl sulfonylflouride). Nuclei and debris were removed by centrifugation and then the cell extract was cromatographed on heparin-sepharose (HS) as described in Moscatelli, supra, which is incorporated herein by this reference. A 3M NaCl HS eluate contained the hmwbFGF's. Following standard procedures, fractions collected were separated on 12% SDS-PAGE, and analyzed following Western-blotting to nitrocellulose with the indicated affinity-purified anti-FGF antibodies as described by Szewcbyk et al. *Analytical Bioch.* 1985, Vol. 150, pgs 403–407, which is incorporated herein by this reference. This procedure indicated the presence of three distinct hmwbFGF proteins corresponding to molecular weights of 22 kD, 23 kD and 24 kD in addition to the bFGF-18 angiogenic factor.

EXAMPLE 2

In vitro translation of RNA transcribed from naturally occurring bFGF cDNA

RNA-dependent in vitro translations were performed in wheat germ extracts in the presence of $^{35}$S-methionine according to procedures as described by Pelham et al. *Eur. J. Biochem.*, 1976, Vol. 67, page 247, which is incorporated herein by this reference, with subsequent immunoprecipitations performed as described by Florkiewicz et al, *J. Cell Biology* 1983, Vol. 97, pages 1381–1388, which is incorporated herein by this reference. Immunoprecipitated samples were eluted from protein-A sepharose and resolved on 12% SDS-PAGE, and visualized by fluorography. Again, proteins of molecular weights 18, 22, 23 and 24 kD were detected. This procedure yields hmwbFGF's substantially free of human proteins that are not angiogenic factors.

EXAMPLE 3

Mutations of bFGF cDNA clone to determine initiation sites

Site-directed oligonucleotide mutations at positions 201 (CTG to CTT) and 365 (ATG to GCT) were introduced into bFGF cDNA clones using a Biorad mutagene kit following procedures as described by Kunkel et al. *Methods in Enzymol,* 1987, Vol. 154, pp. 367–382, which is incorporated herein by this reference. A nucleic acid sequence containing a mutation at position 243 (CTG to CTT) was obtained by re-synthesizing a fragment of DNA (using four overlapping synthetic oligonucleotides) between the XhoI site at nucleotide 192 and the ApaI site at nucleotide 353.

The mutagenized cDNAs, contained within the hybrid expression vector pJCl19, were transfected into COS-1 cells as described by Machamer et al., *Mol. Cell Bio.*, 1985, Vol. 5, pp. 3074–3083, which is incorporated herein by this reference. 40–48 hours after transfection, cells were lysed as described above in example 1 and the extracts were incubated with HS for 2 hours at 4° C. The HS pellets were washed with buffer containing 0.5M NaCl and 20 mM Tris pH 7.5, then three times with 1M NaCl and 20 mM Tris pH 7.5 buffer solution. The pellets were then eluted with 3M NaCl buffer and the eluant analyzed by SDS-PAGE and Western blotting using affinity-purified anti-bFGF antibodies.

Translation occurring from these mutagenized oligonucleotides produced proteins which were isolated and identified as described above in example 1. The oligonucleotide mutated at position 201 produced bFGF-18, bFGF-22 and bFGF-23. The oligonucleotide with a mutation at position 243 produced bFGF-18, bFGF-23 and bFGF-24. And finally, the oligonucleotide with a mutation at position 365 yielded all three hmwbFGFs, bFGF-22, bFGF-23 and bFGF-24, free of bFGF.

EXAMPLE 4

Frame-shift mutation of bFGF clone to determine mitogenic active site

The frame-shift mutation, effectively adding a single nucleic acid between positions 353 and 354 (the unique ApaI site), is performed by treatment of the bFGF cDNA clone with the oligonucleotide 5'GGCCTCTAGAGCCGGCC3' according to standard procedures. Translation products of this oligonucleotide were observed by transfecting the clones into COS-1 cells as described above in example 3, and the resulting proteins were analyzed as described above in example 1. No proteins reactive to anti-bFGF antibodies were detected from translation of this mutated sequence.

EXAMPLE 5

Mitoaenic assay of hmwbFGF's

HS pellets prepared as described above in example 3 containing the lysate from cells transfected with naturally occurring bFGF cDNA and an oligonucleotide mutated at position 365 were eluted with buffer containing 3M NaCl. Aliguots of these eluants were assayed directly in the 3T3 cell mitogenicity assay as described by Presta et al., *Mol. Cell Biol.*, 1986, Vol. 6, pp. 4060–4066 which is incorporated herein by this reference, measuring incorporation of 3H-thymidine into TCA-precipitable counts. The results of this experiment indicted that the hmwbFGF's had nearly identical mitogenicity properties as the bFGF angiogenic factor. Quantitative western blot analysis of these samples indicated bFGF concentrations of 1 ng/uL of 3M NaCl eluate.

We claim:

1. A purified CTG-initiated high molecular weight

L—G—G—R—G—R—G—R—A—P—E—R—V—G—G—R—G—R—G—R—C—T—A—A—P—R—A—A—P—A—A—R—G—S—
R—P—G—P—A—G—T—M—A—A—G—S—I—T—T—L—P—A—L—P—E—D—G—G—S—G—A—F—P—P—G—H—F—K—D—
P—K—R—L—Y—C—K—N—G—F—F—L—R—I—H—P—D—G—R—V—D—G—V—R—E—K—S—D—P—H—I—K—L—
Q—L—Q—A—E—E—R—G—V—V—S—I—K—G—V—C—A—N—R—Y—L—A—M—K—E—D—G—R—L—L—A—S—K—C—
V—T—D—E—C—F—F—F—E—R—L—E—S—N—N—Y—N—T—Y—R—S—R—K—Y—T—S—W—Y—V—A—L—K—R—T—
G—Q—Y—K—L—G—S—K—T—G—P—G—Q—K—A—I—L—F—L—P—M—S—A—K—S.

form of human bFGF-18, selected from the group consisting of bFGF-22, bFGF-23, and bFGF-24, wherein said high molecular weight form has at least one active site possessing mitogenic activity.

2. The purified CTG-initiated high molecular weight form of human bFGF-18 of claim 1 comprising an amino acid sequence of:

M—A—A—G—S—I—T—T—L—P—A—L—P—E—D—G—G—S—G—A—
F—P—P—G—H—F—K—D—P—K—R—L—Y—C—K—N—G—G—F—F—
L—R—I—H—P—D—G—R—V—D—G—V—R—E—K—S—D—P—H—I—
K—L—Q—L—Q—A—E—E—R—G—V—V—S—I—K—G—V—C—A—N—
R—Y—L—A—M—K—E—D—G—R—L—L—A—S—K—C—V—T—D—E—
C—F—F—F—E—R—L—E—S—N—N—Y—N—T—Y—R—S—R—K—Y—
T—S—W—Y—V—A—L—K—R—T—G—Q—Y—K—L—G—S—K—T—G—
P—G—Q—K—A—I—L—F—L—P—M—S—A—K—S.

3. The purified CTG-initiated high molecular weight form of human bFGF-18 of claim 2, wherein said high molecular weight form is bFGF-22, and comprises the amino acid sequence of:

4. The purified CTG-initiated high molecular weight form of human bFGF-18 of claim 2, wherein said high molecular weight form is bFGF-23, and comprises the amino acid sequence of:

L—P—G—G—R—L—G—R—G—R—G—R—A—P—E—R—V—G—G—R—G—R—G—R—C—T—A—A—P—R—A—A—P—
A—A—R—G—S—R—P—G—P—A—G—T—M—A—A—G—S—I—T—T—L—P—A—L—P—E—D—G—G—S—G—A—F—P—P—
G—H—F—K—D—P—K—R—L—Y—C—K—N—G—F—F—L—R—I—H—P—D—G—R—V—D—G—V—R—E—K—S—D—
P—H—I—K—L—Q—L—Q—A—E—E—R—G—V—V—S—I—K—G—V—C—A—N—R—Y—L—A—M—K—E—D—G—R—L—
L—A—S—K—C—V—T—D—E—C—F—F—F—E—R—L—E—S—N—N—Y—N—T—Y—R—S—R—K—Y—T—S—W—Y—V—
A—L—K—R—T—G—Q—Y—K—L—G—S—K—T—G—P—G—Q—K—A—I—L—F—L—P—M—S—A—K—S.

5. The purified CTG-initiated high molecular weight form of human bFGF-18 of claim 2, wherein said high molecular weight form is bFGF-24, and comprises the amino acid sequence of:

L—G—A—R—G—R—A—L—P—G—G—R—L—G—G—R—G—R—G—R—A—P—E—R—V—G—G—R—G—R—G—R—C—T—
A—A—P—R—A—A—P—A—A—R—G—S—R—P—G—P—A—G—T—M—A—A—G—S—I—T—T—L—P—A—L—P—E—D—
G—G—S—G—A—F—P—P—G—H—F—K—D—P—K—R—L—Y—C—K—N—G—F—F—L—R—I—H—P—D—G—R—V—
D—G—V—R—E—K—S—D—P—H—I—K—L—Q—L—Q—A—E—E—R—G—V—V—S—I—K—G—V—C—A—N—R—Y—L—
A—M—K—E—D—G—R—L—L—A—S—K—C—V—T—D—E—C—F—F—F—E—R—L—E—S—N—N—Y—N—T—Y—R—S—
R—K—Y—T—S—W—Y—V—A—L—K—R—T—G—Q—Y—K—L—G—S—K—T—G—P—G—Q—K—A—I—L—F—L—P—M—
S—A—K—S.

* * * * *